(12) United States Patent
Koepsel et al.

(10) Patent No.: US 11,406,102 B2
(45) Date of Patent: Aug. 9, 2022

(54) TISSUE CONTAINER SYSTEMS

(71) Applicant: Stratatech Corporation, Madison, WI (US)

(72) Inventors: Justin Koepsel, Madison, WI (US); Ken Gratz, Madison, WI (US)

(73) Assignee: Stratatech Corporation, Madison, WI (US)

( * ) Notice: Subject to any disclaimer, the term of this patent is extended or adjusted under 35 U.S.C. 154(b) by 117 days.

(21) Appl. No.: 16/481,405

(22) PCT Filed: Jan. 26, 2018

(86) PCT No.: PCT/US2018/015490
§ 371 (c)(1),
(2) Date: Jul. 26, 2019

(87) PCT Pub. No.: WO2018/140755
PCT Pub. Date: Aug. 2, 2018

(65) Prior Publication Data
US 2020/0128815 A1  Apr. 30, 2020

Related U.S. Application Data

(60) Provisional application No. 62/451,379, filed on Jan. 27, 2017.

(51) Int. Cl.
*A01N 1/02* (2006.01)
*C12M 1/12* (2006.01)

(52) U.S. Cl.
CPC ......... *A01N 1/0268* (2013.01); *A01N 1/0221* (2013.01); *A01N 1/0273* (2013.01); *C12M 23/04* (2013.01)

(58) Field of Classification Search
CPC .. A01N 1/0268; A01N 1/0221; A01N 1/0273; C12M 23/04
See application file for complete search history.

(56) References Cited

U.S. PATENT DOCUMENTS 3,862,886 A * 1/1975 Liner ..................... C12M 23/14
                                                          435/299.1
4,883,452 A   11/1989 Kasai et al.
5,508,005 A * 4/1996 Mathus ................. B01L 3/5085
                                                          422/551
(Continued)

FOREIGN PATENT DOCUMENTS

CN    1589622 A    3/2005
GB    2113249 A    8/1983
(Continued)

OTHER PUBLICATIONS

Extended European Search Report for EP18744799.0 dated Nov. 13, 2020, 7 pages.
(Continued)

*Primary Examiner* — William H. Beisner
*Assistant Examiner* — Danielle B Henkel

(57) ABSTRACT

The present invention relates generally to tissue container systems that find use in the transport of tissues and methods of using the tissue container systems. In particular the present invention relates to systems that support the transport, thawing and use of cryopreserved human skin equivalents, and methods of their use by a health care provider.

24 Claims, 6 Drawing Sheets

(56) References Cited

U.S. PATENT DOCUMENTS

| | | | |
|---|---|---|---|
| 5,964,096 A | 10/1999 | Watson et al. | |
| 2002/0175164 A1 | 11/2002 | Dees et al. | |
| 2003/0215940 A1* | 11/2003 | Lacey | C12M 23/12 435/305.2 |
| 2008/0237228 A1 | 10/2008 | Chou | |
| 2009/0145087 A1 | 6/2009 | Allen-Hoffman et al. | |
| 2015/0099044 A1 | 4/2015 | Bowa | |

FOREIGN PATENT DOCUMENTS

| | | |
|---|---|---|
| GB | 2113249 B | 3/1985 |
| JP | S5926032 A | 2/1984 |
| JP | S60152603 U | 10/1985 |
| JP | H11501298 A | 2/1999 |
| JP | 2015524918 A | 8/2015 |
| JP | 2016178946 A | 10/2016 |
| WO | 9624018 A1 | 8/1996 |
| WO | 2008030961 A1 | 3/2008 |
| WO | 2013192607 A1 | 12/2013 |

OTHER PUBLICATIONS

International Search Report and Written Opinion for PCT/US2018/015490 dated Apr. 9, 2018, 8 pages.

Office Action for CN Application No. 201880008065.7 dated Feb. 3, 2020, 16 pages.

International Preliminary Report on Patentability for International Application No. PCT/US2018/015490, dated Aug. 8, 2019, 7 pages.

Office Action for Japanese Patent Application No. 20190538639, dated Sep. 27, 2021, 11 Pages.

Second Office Action for Chinese Patent Application No. 201880008065.7, dated Aug. 3, 2021, 22 Pages.

* cited by examiner

TISSUE CONTAINER SYSTEMS

CROSS REFERENCE TO RELATED APPLICATIONS

This application claims priority to PCT/US2018/015490, filed Jan. 26, 2018, which claims the benefit of U.S. provisional application number 62/451,379, filed Jan. 27, 2017, which is hereby incorporated by reference in its entirety.

FIELD OF THE INVENTION

The present invention relates generally to tissue container systems that find use in the transport of tissues and methods of using the tissue container systems. In particular the present invention relates to systems that support the transport, thawing and use of cryopreserved human skin equivalents, and methods of their use by a health care provider.

BACKGROUND OF THE INVENTION

A major impediment to the acceptance of engineered tissues by medical practitioners, healthcare providers, and second party payers is the lack of a means to effectively and efficiently preserve and store engineered tissues. The nature of living cells and tissue products makes development of long-term storage challenging. Current engineered tissues must often be stored and shipped under carefully controlled conditions to maintain viability and function. Typically, engineered tissue products take weeks or months to produce but must be used within hours or days after manufacture. As a result, tissue engineering companies must continually operate with their production facilities at top capacity and absorb the costs of unsold product which must be discarded. As one specific example, APLIGRAF requires about four weeks to manufacture, is usable for only 15 days and must be maintained between 20 and 23° C. until used. As another example, EPICEL is transported by a nurse from Genzyme Biosurgery's production facility in Cambridge, Mass. to the point of use in a portable incubator and is used immediately upon arrival. Such constraints represent significant challenges to developing convenient and cost-effective products.

Cryopreservation has been explored as a solution to the storage problem, but it is known to induce tissue damage through ice formation, chilling injury, and osmotic imbalance. Besides APLIGRAF, the only other approved full-thickness living skin equivalent, ORCEL, has been evaluated as a frozen product but had the drawback that it must be maintained at temperatures below −100° C. prior to use. This requires specialized product delivery and storage conditions, including use of liquid nitrogen for storage, which is expensive and not readily available in rural clinics and field hospitals.

Accordingly, what is needed in the art are improved methods of cryopreserving viable engineered tissues and cells for storage under conditions that are routinely available at the point of use.

SUMMARY OF THE INVENTION

The present invention relates generally to tissue container systems that find use in the transport of tissues and their subsequent use by a health care provider, and in particular to systems that support the transport, thawing and use of cryopreserved human skin equivalents.

Accordingly, in some embodiments, the present invention provides tissue containers comprising: a perimeter wall and a substantially planar bottom surface defining a dish, the perimeter wall having a male end and a female end, the male end of the perimeter wall having projecting therefrom a ridge having a length and width, wherein the female end of the perimeter wall defines a space corresponding to the length and width of the ridge so that when an identical tissue container is placed on top of the tissue container the female end of the tissue container releasably receives the ridge extending from the male end of the identical tissue container, and the bottom surface having a perimeter and comprising a perimeter ledge extending around the perimeter to provide a reservoir defined by the perimeter ledge and the bottom surface. In some embodiments, the perimeter wall has a flange extending therefrom. In some embodiments, the flange comprises one or more tabs extending from the male end of the perimeter wall. In some embodiments, the flange comprises one or more tabs extending from the female end of the perimeter wall. In some embodiments, the ridge has a proximal end and the proximal end of the ridge has one or more indents therein.

In some embodiments, the present invention provides tissue container assemblies comprising: substantially identical top and bottom tissue containers, each of the top and bottom tissue containers comprising a perimeter wall and a substantially planar bottom surface defining a dish, the bottom surface having a perimeter and comprising a perimeter ledge extending around the perimeter to provide a reservoir defined by the perimeter ledge and the bottom surface, and the perimeter wall having a male end and a female end, the male end of the perimeter wall having projecting therefrom a ridge having a length and width, wherein the female end of the perimeter wall defines a space corresponding to the length and width of the ridge so that when the top tissue container is placed on the bottom tissue container the female end of the bottom tissue container releasably receives the ridge extending from the male end of the top tissue container. In some embodiments, the perimeter wall of the top tissue container has a top flange extending therefrom and the perimeter wall of the bottom tissue container has a bottom flange extending therefrom so that when the top and bottom tissue containers are assembled the top and bottom flanges contact one another. In some embodiments, the top flange comprises one or more tabs extending from the male end of the perimeter wall and one or more tabs extending from the female end of the perimeter wall. In some embodiments, the bottom flange comprises one or more tabs extending from the male end of the perimeter wall and one or more tabs extending from the female end of the perimeter wall. In some embodiments, the bottom flange comprises one or more tabs extending from the male end of the perimeter wall and one or more tabs extending from the female end of the perimeter wall and the wherein the top flange comprises one or more tabs extending from the male end of the perimeter wall and one or more tabs extending from the female end of the perimeter wall so that when the top and bottom tissue containers are assembled the tabs are offset.

In some embodiments, the present invention provides tissue container systems comprising: substantially identical top and bottom tissue containers and a tray comprising a porous bottom surface, each of the top and bottom tissue containers comprising a perimeter wall and a substantially planar reservoir bottom surface defining a dish, the reservoir bottom surface having a perimeter and comprising a perimeter ledge extending around the perimeter to provide a reservoir defined by the perimeter ledge and the reservoir bottom surface, wherein the tray is sized to be supported by the ledge and above the reservoir bottom surface when inserted into the tissue container, and the perimeter wall having a male end and a female end, the male end of the perimeter wall having projecting therefrom a ridge having a length and width, wherein the female end of the perimeter wall defines a space corresponding to the length and width of the ridge so that when the top tissue container is placed on the bottom tissue container the female end of the bottom tissue container releasably receives the ridge extending from the male end of the top tissue container. In some embodiments, the perimeter wall of the top tissue container has a top flange extending therefrom and the perimeter wall of the bottom tissue container has a bottom flange extending therefrom so that when the top and bottom tissue containers are assembled the top and bottom flanges contact one another. In some embodiments, the top flange comprises one or more tabs extending from the male end of the perimeter wall and one or more tabs extending from the female end of the perimeter wall. In some embodiments, the bottom flange comprises one or more tabs extending from the male end of the perimeter wall and one or more tabs extending from the female end of the perimeter wall. In some embodiments, the bottom flange comprises one or more tabs extending from the male end of the perimeter wall and one or more tabs extending from the female end of the perimeter wall and the wherein the top flange comprises one or more tabs extending from the male end of the perimeter wall and one or more tabs extending from the female end of the perimeter wall so that when the top and bottom tissue containers are assembled the tabs are offset. In some embodiments, the porous bottom surface of the tray is a porous membrane. In some embodiments, the ridge has a proximal end and the proximal end of the ridge has one or more indents therein and the tray has one or more tray tabs so that when the tray is inserted into the bottom tissue container the one or more tabs are inserted into the one or more indents. In some embodiments, the systems further comprise a tissue supported on the porous bottom surface of the tray. In some embodiments, the tissue is cryopreserved. In some embodiments, the tissue is an organotypic skin substitute. In some embodiments, the systems further comprise a sterile package containing the tissue container system. The tissue container system can be provided as a kit with one or more absorbent medium and/or one or more liquid media, such as a tissue compatible solution.

In some embodiments, the present invention provides methods of providing a tissue for use by a health care provider comprising packaging a tissue in the tissue container system of the preceding paragraph and providing the packaged tissue to a health care provider in need thereof. In some embodiments, the present invention provides methods of thawing a cryopreserved tissue comprising: providing a cryopreserved tissue in the tissue container system as described above, removing the top tissue container to expose the cryopreserved tissue, optionally transferring the cryopreserved tissue to a new container system, and filling the reservoir in the bottom tissue container with a liquid medium under conditions that the cryopreserved tissue thaws to provide a thawed tissue. In some embodiments, the cryopreserved tissue is an organotypic human skin substitute. In some embodiments, the methods further comprise applying or grafting the organotypic human skin substitute to a burn or a wound on a patient in need thereof.

In some embodiments, the present invention provides a tissue container 100 shown in FIG. 1 that comprises a perimeter wall 105 and a substantially planar bottom surface 110 defining a dish. The perimeter wall 105 has a male end 115 and a female end 120. The male end 115 of the perimeter wall 105 has a ridge 125 extending therefrom that has a length and a width. The female end 120 of the perimeter wall 105 defines a space 130 corresponding to the length and width of the ridge 125 so that when an identical tissue container is placed on top of the tissue container 100 the space 130 provided in said female end 120 of the tissue container can releasably receive the ridge 125 extending from the male end of the identical tissue container as shown in more detail below. The bottom surface 110 comprises a perimeter ledge 135 extending around the perimeter of the bottom surface 110. The perimeter ledge 135 forms a reservoir 140 on the bottom of the container that is preferably about 0.50 to 1.5 mm deep, and most preferably about 0.75 mm deep and which can be filled with a liquid medium. The perimeter wall 105 preferably has a flange 145 extending therefrom. In some embodiments, the tissue container 100 further comprises (a) a flange 145 comprising one or more tabs 150 extending the male end 115 and female end 120 of the perimeter wall, (b) a ridge 125 that has one more indents 155 therein that are configured to receive tabs on a tray, (c) a perimeter wall 105 comprising a plurality of grip projections 160, preferably positioned on the male end 115 of the perimeter wall 105, or (d) any combination thereof. The present invention also provides a tissue container assembly comprising substantially identical bottom and top containers, wherein the bottom and top containers are a tissue container described in this paragraph. The present invention also provides a tissue container system shown in FIG. 4 comprising a tissue container assembly of this paragraph and a tray 410. The tray is sized so that it rests on top of the perimeter ledge on the bottom surface of the bottom container as described above. The tray 410 comprises sidewalls 415. Tabs 420 extend from the sidewalls 415 so that they engage and are inserted into indents 425 in the ridge 430 on the male end 435 of the bottom container 405. The tray has a porous bottom surface 440, which is optionally a porous membrane. An identical top container can be placed on the bottom container and closed, without interference from the contained tray. The tissue container system can be optionally sealed, preferably heat sealed, in a sterile bag to provide a primary package. The primary package can be optionally sealed inside a secondary bag. The tissue container system or package containing the tissue container system can be provided as a kit with one or more absorbent medium and/or one or more liquid media, such as a tissue compatible solution.

In some embodiments, the present invention provides methods of providing a tissue for use by a health care provider comprising packaging a tissue in the tissue container system as described in the preceding paragraph and providing the packaged tissue to a health care provider in need thereof. In some embodiments, the present invention provides methods of providing a tissue for use to treat a wound or a burn comprising packaging a tissue in the tissue container system as described in the preceding paragraph and providing the packaged tissue to a health care provider for use to treat wound or a burn. In some embodiments, the present invention provides a method of thawing a cryopreserved skin equivalent prior to application to a subject. The method comprises providing a cryopreserved tissue, preferably an organotypically cultured skin equivalent, in a tissue container system as described in the preceding paragraph, removing the top tissue container to expose the cryopreserved tissue, and filling the reservoir in the bottom tissue container with a liquid medium under conditions that the cryopreserved tissue thaws to provide a thawed tissue, where the cryoprotectant contained within the tissue is diluted into the liquid medium, leaving a tissue that is substantially free of cryoprotectant. In other embodiments, the method comprises removing a primary or secondary package containing a tissue container system comprising a cryopreserved tissue from a freezer or shipping container, removing the tissue container system from the package(s), removing the top tissue container to expose the cryopreserved tissue, and transferring the tray with the cryopreserved skin equivalent from the first tissue container into a second tissue container that is sterile and staged in the sterile field and contains a liquid medium in the container reservoir, such that the transferred cryopreserved tissue thaws to provide a thawed tissue and the cryoprotectant contained within the tissue is diluted into the liquid medium. In some of the above embodiments, the liquid medium is a tissue compatible solution, preferably a buffered solution. In still other embodiments, the tray with the cryopreserved skin equivalent is removed from the tissue container and placed on an absorbent medium to remove thawed cryoprotectant solution from the skin equivalent. The absorbent medium may be in any suitable, preferably sterile, vessel (e.g., a culture vessel or a fresh tissue container assembly). The present invention is not limited to the use of a particular absorbent medium. The absorbent medium preferably comprises a tissue-compatible solution.

Other aspects and iterations of the invention are described more thoroughly below.

DETAILED DESCRIPTION

Figure 1:
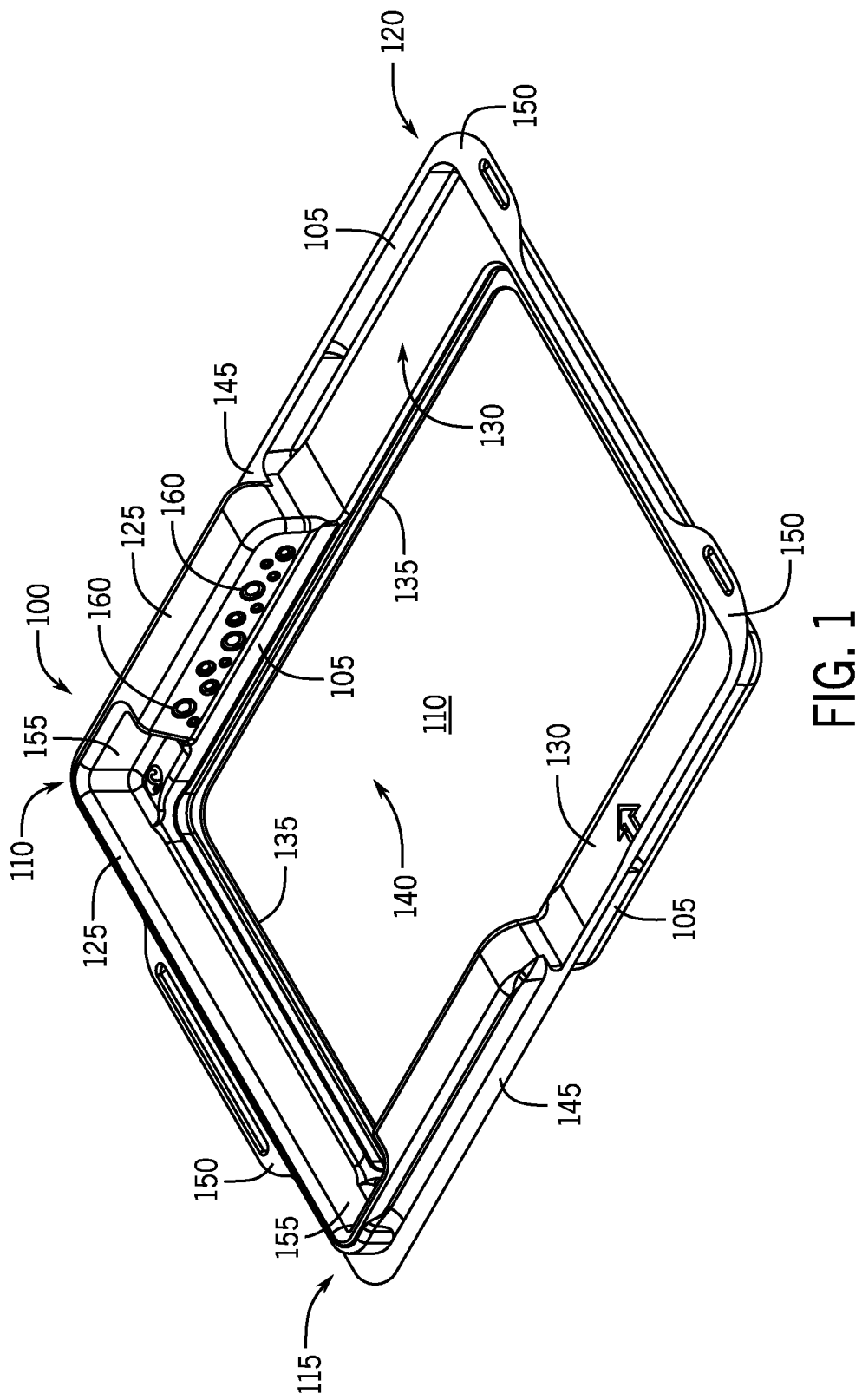
FIG. 1 is a perspective view of a tissue container in accordance with one embodiment.

The present invention relates generally to tissue container systems that find use in the transport of tissues and their subsequent use by a health care provider, and in particular to systems that support the transport, thawing and use of cryopreserved human skin equivalents.

As used herein, the terms "skin equivalent," "human skin equivalent," "human skin substitute," and "organotypic human skin equivalent" are used interchangeably to refer to an in vitro derived culture of keratinocytes that has stratified into squamous epithelia. Typically, the skin equivalents are produced by organotypic culture and include a dermal layer in addition to a keratinocyte layer.

As used herein, the term "sterile" refers to a skin equivalent that is essentially or completely free of detectable microbial or fungal contamination.

As used herein, the term "NIKS cells" refers to cells having the characteristics of the cells deposited as cell line ATCC CRL-12191. "NIKS" stands for near-diploid immortalized keratinocytes and is a registered trademark.

As used herein, the term "viable" when used in reference to a skin equivalent refers to the viability of cells in the skin equivalent following cryopreservation. In preferred embodiments, a "viable" skin has an A550 of at least 50%, 60%, 70%, 80% or 90% of a control non-cryopreserved tissue as measured by an MTT assay or at least 50%, 60%, 70%, 80% or 90% of the readout value of a similar viability assay.

As used herein, the term "culture vessel" refers to any vessel of the type commonly used to culture cells or tissues and includes circular, rectangular, and square dishes formed from a suitable material such as tissue culture plastic, polystyrene, polymers, plastics, glass, etc. The term "culture vessel" and "growth chamber" are used interchangeably. Tissue containers of the present disclosure are not culture vessels, as used herein, at least because the tissue containers of the present disclosure are not of a suitable size for long-term culture.

The tissue containers of the instant invention make efficient use of freezer and surgical suite space as they are approximately 60% smaller than previously utilized containers. The tissue containers are compatible with a tray that includes a porous membrane as bottom surface upon which a tissue (e.g., an organotypic skin substitute) can be supported. The other surfaces of the tray are preferably clear or translucent plastics produced by a thermoforming process from a plastic sheet, injection molding, or other methods known in the art to manipulate plastics. Suitable plastics include medical grade plastics, for example, polyethylene terephthlate glycol-modified (PETG), polystyrene, etc. In some preferred embodiments, the tray is a preferably a tray as described in paragraph [0030] herein. The tissue containers include a reservoir that can be filled with media to thaw the tissue in the container and remove cryoprotectant when the tissue has been frozen. This provides an advantage over previous systems used for thawing tissues where the tissue had to be removed from the container in the surgical sterile field and then placed on a Telfa® pad. The tissue containers of the present invention preferably include a top and bottom which are mirror images of one another. The top and bottom pieces of the container assembly are substantially identical and can be snapped together to form an enclosed container. The use of a top and bottom which are substantially identical means that both the top and bottom piece can be produced from the same molds, which creates efficiencies during the production of the top and bottom pieces. The top and bottom pieces are preferably clear and produced by a thermoforming process from a plastic sheet. Suitable plastics include medical grade thermoformable plastics, for example, polyethylene terephthlate glycol-modified (PETG). Accordingly, the present invention provides improved tissue containers and tissue container systems which will be described in more detail below.

FIG. 1 shows a tissue container 100. In some embodiments, the tissue container 100 preferably comprises a perimeter wall 105 and a substantially planar bottom surface 110 defining a dish. The perimeter wall 105 has a male end 115 and a female end 120. The male end 115 of the perimeter wall 105 has a ridge 125 extending therefrom that has a length and a width. The female end 120 of the perimeter wall 105 defines a space 130 corresponding to the length and width of the ridge 125 so that when an identical tissue container is placed on top of the tissue container 100 the space 130 provided in said female end 120 of the tissue container can releasably receive the ridge 125 extending from the male end of the identical tissue container as shown in more detail below. The bottom surface 110 comprises a perimeter ledge 135 extending around the perimeter of the bottom surface 110. The perimeter ledge 135 forms a reservoir 140 on the bottom of the container that is preferably about 0.50 to 1.5 mm deep, and most preferably about 0.75 mm deep and which can be filled with a liquid medium. The perimeter wall 105 preferably has a flange 145 extending therefrom. In some embodiments, the flange 145 comprises one or more tabs 150 extending the male end 115 and female end 120 of the perimeter wall. In some embodiments, the ridge 125 has one or more indents 155 therein that are configured to receive tabs on a tray, which is shown in more detail below. In some further embodiments the perimeter wall 105 preferably comprises a plurality of grip projections 160, preferably positioned on the male end 115 of the perimeter wall 105.

Figure 2:
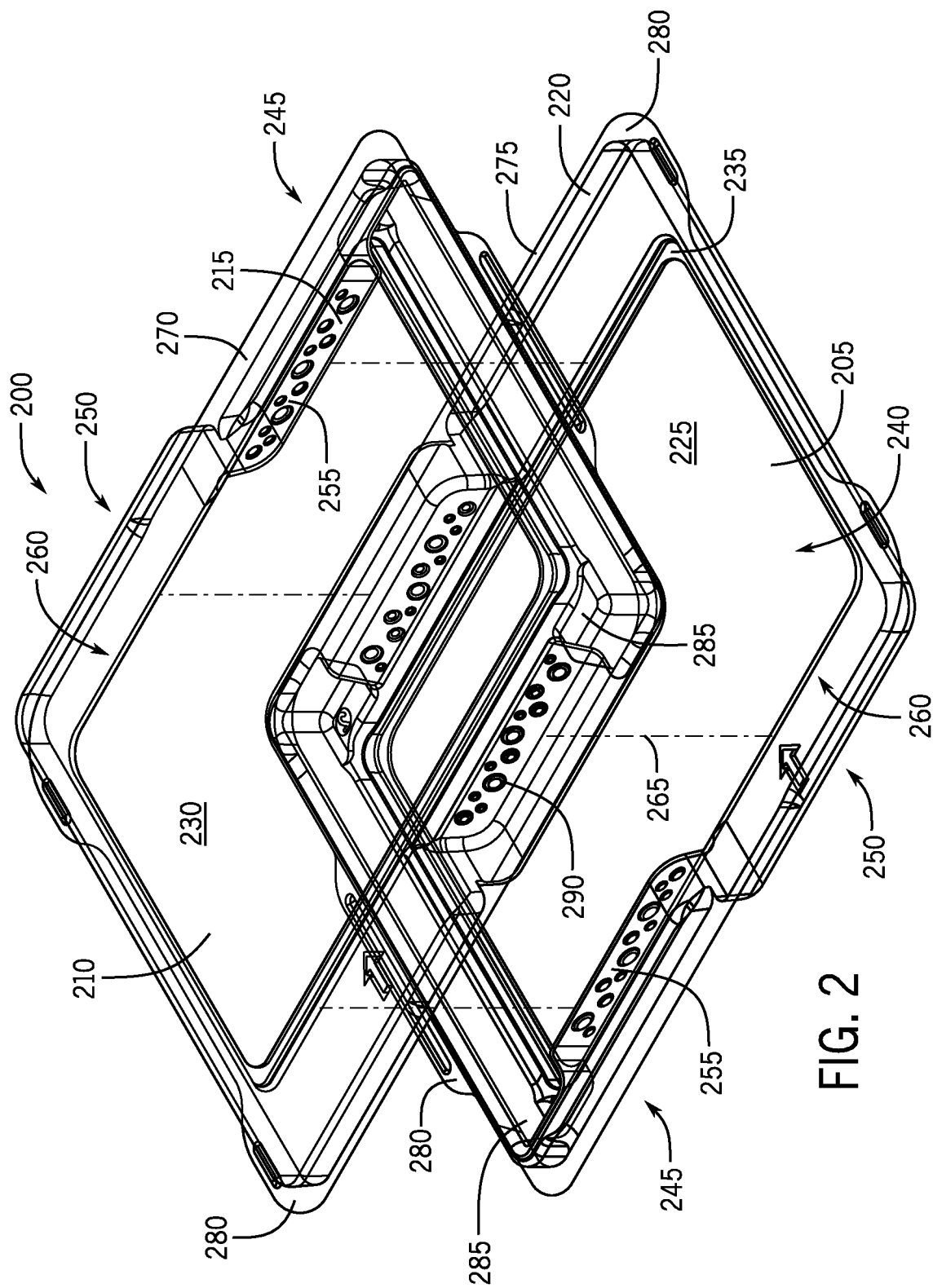
FIG. 2 is disassembled perspective view of a tissue container assembly according to one embodiment.
Figure 3:
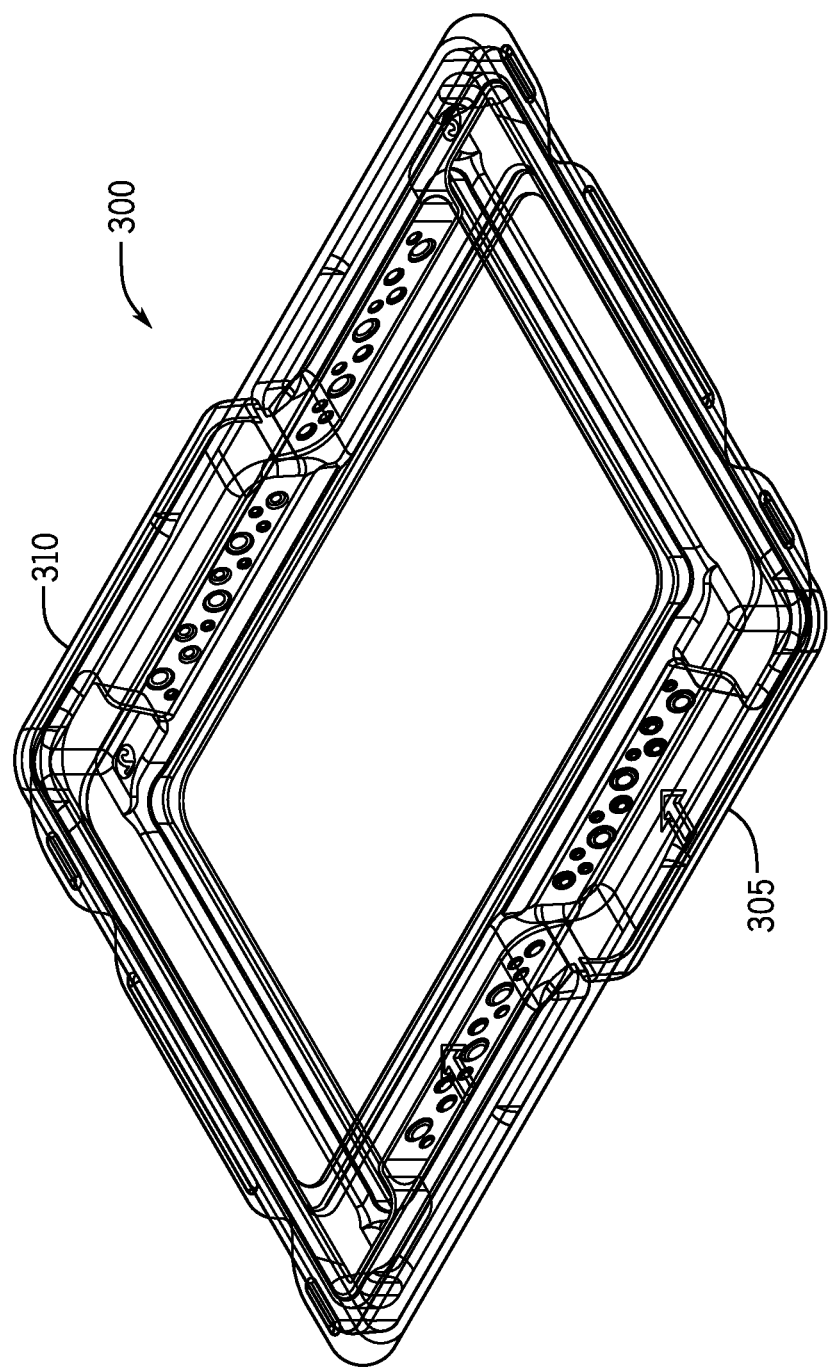
FIG. 3 is a perspective view of an assembled tissue container assembly accordingly to one embodiment.

FIG. 2 shows an expanded view of a tissue container assembly 200 of the instant invention. The tissue container assembly 200 preferably comprises substantially identical bottom and top containers 205 and 210. Each of the bottom and top containers 205 and 210 comprise a perimeter wall 215 and 220 and have a bottom surface 225 in the case of the bottom container 205 and a top surface 230 in the case of the top container 210. The bottom surface 225 comprises a perimeter ledge 235 extending around the perimeter of the bottom surface 225. The perimeter ledge 235 forms a reservoir 240 on the bottom of the bottom container 205 that is preferably about 0.50 to 1.5 mm deep, and most preferably about 0.75 mm deep and which can be filled with a liquid medium. Each of the bottom and top containers 205 and 210 comprise male and female ends 245 and 250. The male ends 245 have a ridge 255 extending therefrom that has a length and a width. The female ends 250 define a space 260 corresponding to the length and width of the ridges 255 so that when the top container 210 is placed on the bottom container 205 along the alignment shown by dashed lines 265 the space 260 provided in said female ends 250 of the bottom and top tissue containers 205 and 210 can releasably receive the ridges 255 so that the bottom and top containers 205 and 210 can be releasably snapped together. The perimeter walls 215 and 220 preferably have flanges 270 and 275 extending therefrom. In some embodiments, the flanges comprise one or more tabs 280 extending the male and female ends 245 and 250. In some embodiments, the ridges 255 have one or more indents 285 therein that are configured to receive tabs on a tray, which is shown in more detail below. In some further embodiments the perimeter walls preferably comprises a plurality of grip projections 290, preferably positioned on the male ends 245. FIG. 3 shows a container assembly 300 of the present invention where the bottom container 305 and top container 310 are fully engaged to form an enclosed container.

Figure 4:
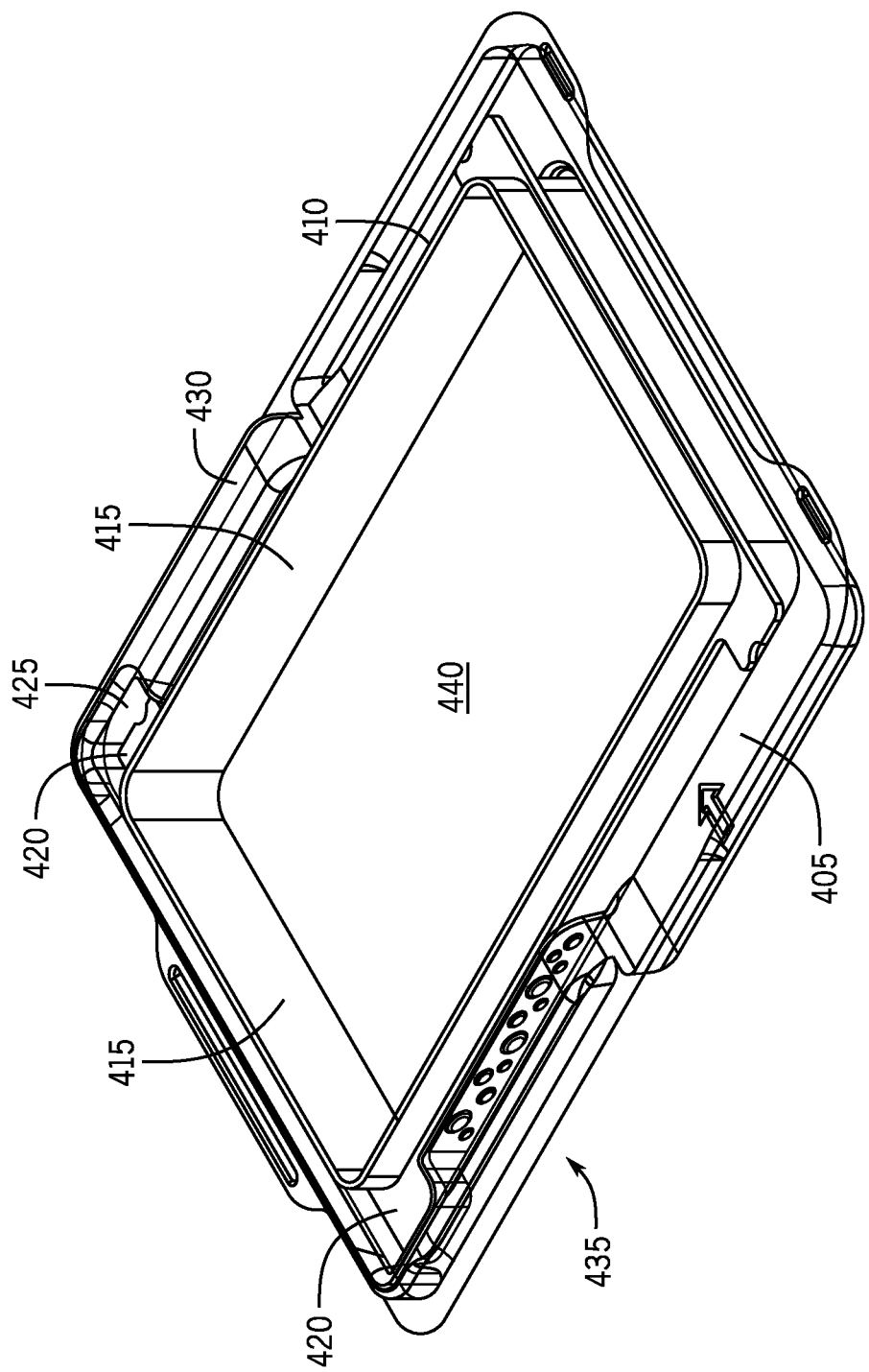
FIG. 4 is a perspective view of a tissue container with an inserted tray according to one embodiment.

The present invention further provides a tissue container system comprising the bottom and top containers described above along with a tray. FIG. 4 shows a bottom container of the present invention into which a tray 410 has been inserted. The tray 410 is sized so that it rests on top of the perimeter ledge on the bottom surface of the bottom container as described above. The tray 410 comprises sidewalls 415. Tabs 420 extend from the sidewalls 415 so that they engage and are inserted into indents 425 in the ridge 430 on the male end 435 of the bottom container 405. Sidewalls 415 and tabs 420 are preferably clear or translucent plastics produced by a thermoforming process from a plastic sheet, injection molding, or other methods known in the art to manipulate plastics. Preferred plastics are medical grade thermoformable plastics including, but not limited to, polyethylene terephthlate glycol-modified (PETG) and polystyrene. In some preferred embodiments, the plastic used for sidewalls 415 and tabs 420 is polystyrene. The tray preferably has a porous bottom surface 440. In some preferred embodiments, the porous bottom surface is a porous membrane, preferably a semi-permeable polymer film, more preferably a semi-permeable track-etched polymer film. The membrane can be tissue culture treated (e.g., plasma treated) to improve cell attachment. In further embodiments, the membrane has a nominal thickness of at least 5 microns, in some example, about 5 microns to about 20 microns, preferably about 10 microns to about 20 microns, more preferably about 10 microns to about 15 microns. In other examples, the membrane has a nominal thickness of about 10 microns. Suitable membrane materials are known in the art and include, but are not limited to, polyethylene terephthalate, polyester, polycarbonate, or any other membrane material used in commercially available, tissue-culture treated inserts (e.g., Transwell®, Snapwell™, etc.) with a multiplicity of open pores therethrough. Preferably the pores have a nominal pore size of about 0.1 micron to about 10 microns, preferably about 0.1 micron to about 0.8 micron, more preferably about 0.2 micron to about 0.8 micron, even more preferably about 0.4 micron, about 0.5 micron, or about 0.6 micron. The membrane preferably has a nominal pore density between about $1 \times 10^8$ and about $4 \times 10^8$ pores per square centimeter, though a wider range is also acceptable. Most preferably, a membrane is formed from polycarbonate having pores with a nominal size of about 0.4 micron and a nominal pore density about $1 \times 10^8$ pores per square centimeter. The membrane may be attached to sidewalls 415 by any suitable method known in the art, for example by heat sealing, sonic welding, solvent bonding, adhesive bonding and the like.

The present invention may be used to cryopreserve, store and/or transport a variety of tissues. The tissues are preferably supported on the porous bottom surface of the tray and are enclosed with a container assembly of the present invention comprising bottom and top containers. In some preferred embodiments, the tissues are cryopreserved. In some embodiments, the tissues are skin tissues, for example, cadaver skin or organotypic skin equivalents. In some exemplary embodiments, the tissues are organotypic skin equivalents or cryopreserved organotypic skin equivalents.

The present invention is not limited to any particular organotypic skin equivalent. Indeed, the present invention contemplates the use of a variety of cell lines and sources that can differentiate into squamous epithelia, including both primary and immortalized keratinocytes. Sources of cells include keratinocytes and dermal fibroblasts biopsied from humans and cavaderic donors (Auger et al, In Vitro Cell. Dev. Biol.—Animal 36:96-103; U.S. Pat. Nos. 5,968,546 and 5,693,332, each of which is incorporated herein by reference), neonatal foreskins (Asbill et al., Pharm. Research 17(9): 1092-97 (2000); Meana et al., Burns 24:621-30 (1998); U.S. Pat. Nos. 4,485,096; 6,039,760; and 5,536,656, each of which is incorporated herein by reference), and immortalized keratinocytes cell lines such as NM1 cells (Baden, In Vitro Cell. Dev. Biol. 23(3):205-213 (1987)), HaCaT cells (Boucamp et al., J. cell. Boil. 106:761-771 (1988)); and NIKS® cells (Cell line BC-1-Ep/SL; U.S. Pat. No. 5,989,837, incorporated herein by reference; ATCC CRL-12191). Each of the mentioned cell lines can be cultured or genetically modified in order to produce a cell line capable of expressing or co-expressing the desired protein(s). In particularly preferred embodiments, NIKS® cells are utilized. The discovery of the novel NIKS® human keratinocyte cell line provides an opportunity to genetically engineer human keratinocytes with non-viral vectors. A unique advantage of the NIKS® cells is that they are a consistent source of genetically-uniform, pathogen-free human keratinocytes. For this reason, they are useful for the application of genetic engineering and genomic gene expression approaches to provide human skin equivalents with enhanced properties over currently available skin equivalents. NIKS® cells, identified and characterized at the University of Wisconsin, are nontumorigenic, karyotypically stable, and exhibit normal growth and differentiation both in monolayer and organotypic culture. NIKS® cells form fully stratified skin equivalents in culture. These cultures are indistinguishable by all criteria tested thus far from organotypic cultures formed from primary human keratinocytes. Unlike primary cells however, NIKS® cells exhibit an extended lifespan in monolayer culture. This provides an opportunity to genetically manipulate the cells and isolate new clones of cells with new useful properties (Allen-Hoffmann et al., J. Invest. Dermatol., 114(3): 444-455 (2000)).

The NIKS® cells arose from the BC-1-Ep strain of human neonatal foreskin keratinocytes isolated from an apparently normal male infant. In early passages, the BC-1-Ep cells exhibited no morphological or growth characteristics that were atypical for cultured normal human keratinocytes. Cultivated BC-1-Ep cells exhibited stratification as well as features of programmed cell death. To determine replicative lifespan, the BC-1-Ep cells were serially cultivated to senescence in standard keratinocyte growth medium at a density of $3 \times 10^5$ cells per 100-mm dish and passaged at weekly intervals (approximately a 1:25 split). By passage 15, most keratinocytes in the population appeared senescent as judged by the presence of numerous abortive colonies which exhibited large, flat cells. However, at passage 16, keratinocytes exhibiting a small cell size were evident. By passage 17, only the small-sized keratinocytes were present in the culture and no large, senescent keratinocytes were evident. The resulting population of small keratinocytes that survived this putative crisis period appeared morphologically uniform and produced colonies of keratinocytes exhibiting typical keratinocyte characteristics including cell-cell adhesion and apparent squame production. The keratinocytes that survived senescence were serially cultivated at a density of $3 \times 10^5$ cells per 100-mm dish. Typically the cultures reached a cell density of approximately $8 \times 10^6$ cells within 7 days. This stable rate of cell growth was maintained through at least 59 passages, demonstrating that the cells had achieved immortality. The keratinocytes that emerged from the original senescencing population are now termed NIKS®. The NIKS® cell line has been screened for the presence of proviral DNA sequences for HIV-1, HIV-2, EBV, CMV, HTLV-1, HTLV-2, HBV, HCV, B-19 parvovirus, HPV-16, SV40, HHV-6, HHV-7, HPV-18 and HPV-31 using either PCR or Southern analysis. None of these viruses were detected.

Chromosomal analysis was performed on the parental BC-1-Ep cells at passage 3 and NIKS® cells at passages 31 and 54. The parental BC-1-Ep cells have a normal chromosomal complement of 46, XY. At passage 31, all NIKS cells contained 47 chromosomes with an extra isochromosome of the long arm of chromosome 8. No other gross chromosomal abnormalities or marker chromosomes were detected. The karyotype of the NIKS® cells has been shown to be stable to at least passage 54.

The DNA fingerprints for the NIKS® cell line and the BC-1-Ep keratinocytes are identical at all twelve loci analyzed demonstrating that the NIKS® cells arose from the parental BC-1-Ep population. The odds of the NIKS® cell line having the parental BC-1-Ep DNA fingerprint by random chance is $4 \times 10^{-16}$. The DNA fingerprints from three different sources of human keratinocytes, ED-1-Ep, SCC4 and SCC13y are different from the BC-1-Ep pattern. This data also shows that keratinocytes isolated from other humans, ED-1-Ep, SCC4, and SCC13y, are unrelated to the BC-1-Ep cells or each other. The NIKS® DNA fingerprint data provides an unequivocal way to identify the NIKS® cell line.

Loss of p53 function is associated with an enhanced proliferative potential and increased frequency of immortality in cultured cells. The sequence of p53 in the NIKS® cells is identical to published p53 sequences (GenBank accession number: M14695). In humans, p53 exists in two predominant polymorphic forms distinguished by the amino acid at codon 72. Both alleles of p53 in the NIKS® cells are wild-type and have the sequence CGC at codon 72, which codes for an arginine. The other common form of p53 has a proline at this position. The entire sequence of p53 in the NIKS® cells is identical to the BC-1-Ep progenitor cells. Rb was also found to be wild-type in NIKS® cells.

Anchorage-independent growth is highly correlated to tumorigenicity in vivo. For this reason, the anchorage-independent growth characteristics of NIKS® cells in agar or methylcellulose-containing medium were investigated. NIKS® cells remained as single cells after 4 weeks in either agar- or methylcellulose-containing medium. The assays were continued for a total of 8 weeks to detect slow growing variants of the NIKS® cells. None were observed.

To determine the tumorigenicity of the parental BC-1-Ep keratinocytes and the immortal NIKS® keratinocyte cell line, cells were injected into the flanks of athymic nude mice. The human squamous cell carcinoma cell line, SCC4, was used as a positive control for tumor production in these animals. The injection of samples was designed such that animals received SCC4 cells in one flank and either the parental BC-1-Ep keratinocytes or the NIKS® cells in the opposite flank. This injection strategy eliminated animal to animal variation in tumor production and confirmed that the mice would support vigorous growth of tumorigenic cells. Neither the parental BC-1-Ep keratinocytes (passage 6) nor the NIKS® keratinocytes (passage 35) produced tumors in athymic nude mice.

NIKS® cells were analyzed for the ability to undergo differentiation in both submerged culture and organotypic culture. Techniques for organotypic culture are described in detail in the examples. In particularly preferred embodiments, the organotypically cultured skin equivalents of the present invention comprise a dermal equivalent formed from collagen or a similar material and fibroblasts. The keratinocytes, for example NIKS® cells or a combination of NIKS® cells and cells from a patient are seeded onto the dermal equivalent and form an epidermal layer characterized by squamous differentiation following the organotypic culture process.

For cells in submerged culture, the formation of cornified envelopes was monitored as a marker of squamous differentiation. In cultured human keratinocytes, early stages of cornified envelope assembly results in the formation of an immature structure composed of involucrin, cystatin-a and other proteins, which represent the innermost third of the mature cornified envelope. Less than 2% of the keratinocytes from the adherent BC-1-Ep cells or the NIKS® cell line produce cornified envelopes. This finding is consistent with previous studies demonstrating that actively growing, subconfluent keratinocytes produce less than 5% cornified envelopes. To determine whether the NIKS® cell line is capable of producing cornified envelopes when induced to differentiate, the cells were removed from adherent culture and suspended for 24 hours in medium made semi-solid with methylcellulose. Many aspects of terminal differentiation, including differential expression of keratins and cornified envelope formation can be triggered in vitro by loss of keratinocyte cell-cell and cell-substratum adhesion. The NIKS® keratinocytes produced as many as and usually more cornified envelopes than the parental keratinocytes. These findings demonstrate that the NIKS® keratinocytes are not defective in their ability to initiate the formation of this cell type-specific differentiation structure.

To confirm that the NIKS® keratinocytes can undergo squamous differentiation, the cells were cultivated in organotypic culture. Keratinocyte cultures grown on plastic substrata and submerged in medium replicate but exhibit limited differentiation. Specifically, human keratinocytes become confluent and undergo limited stratification producing a sheet consisting of 3 or more layers of keratinocytes. By light and electron microscopy there are striking differences between the architecture of the multilayered sheets formed in submerged culture and intact human skin. In contrast, organotypic culturing techniques allow for keratinocyte growth and differentiation under in vivo-like conditions. Specifically, the cells adhere to a physiological substratum consisting of dermal fibroblasts embedded within a fibrillar collagen base. The organotypic culture is maintained at the air-medium interface. In this way, cells in the upper sheets are air-exposed while the proliferating basal cells remain closest to the gradient of nutrients provided by diffusion through the collagen gel. Under these conditions, correct tissue architecture is formed. Several characteristics of a normal differentiating epidermis are evident. In both the parental cells and the NIKS® cell line a single layer of cuboidal basal cells rests at the junction of the epidermis and the dermal equivalent. The rounded morphology and high nuclear to cytoplasmic ratio is indicative of an actively dividing population of keratinocytes. In normal human epidermis, as the basal cells divide they give rise to daughter cells that migrate upwards into the differentiating layers of the tissue. The daughter cells increase in size and become flattened and squamous. Eventually these cells enucleate and form cornified, keratinized structures. This normal differentiation process is evident in the upper layers of both the parental cells and the NIKS® cells. The appearance of flattened squamous cells is evident in the upper epidermal layers and demonstrates that stratification has occurred in the organotypic cultures. In the uppermost part of the organotypic cultures the enucleated squames peel off the top of the culture. To date, no histological differences in differentiation at the light microscope level between the parental keratinocytes and the NIKS® keratinocyte cell line grown in organotypic culture have been observed.

To observe more detailed characteristics of the parental (passage 5) and NIKS® (passage 38) organotypic cultures and to confirm the histological observations, samples were analyzed using electron microscopy. Parental cells and the immortalized NIKS® human keratinocyte cell line were harvested after 15 days in organotypic culture and sectioned perpendicular to the basal layer to show the extent of stratification. Both the parental cells and the NIKS® cell line undergo extensive stratification in organotypic culture and form structures that are characteristic of normal human epidermis. Abundant desmosomes are formed in organotypic cultures of parental cells and the NIKS® cell line. The formation of a basal lamina and associated hemidesmosomes in the basal keratinocyte layers of both the parental cells and the cell line was also noted.

Hem idesmosomes are specialized structures that increase adhesion of the keratinocytes to the basal lamina and help maintain the integrity and strength of the tissue. The presence of these structures was especially evident in areas where the parental cells or the NIKS® cells had attached directly to the porous support. These findings are consistent with earlier ultrastructural findings using human foreskin keratinocytes cultured on a fibroblast-containing porous support. Analysis at both the light and electron microscopic levels demonstrate that the NIKS® cell line in organotypic culture can stratify, differentiate, and form structures such as desmosomes, basal lamina, and hem idesmosomes found in normal human epidermis.

In some embodiments, the tissues that are supported on the porous membrane and enclosed with the container assembly are cryopreserved. Where this tissue is a skin equivalent, the cryopreserved skin equivalents are preferably storable at approximately −50 C, −60 C, −70 C, −80 C or colder for an extended period of time such as greater than 1, 2, 3, 4, 5 or 6 months and up to 12 or 24 months without a substantial loss of viability.

In preferred embodiments, all steps of the cryopreservation process prior to product packaging are performed aseptically inside a Class 100 biosafety cabinet in a Class 10,000 cleanroom. In some embodiments, the cryopreservation process comprises treating an organotypically cultured skin equivalent in a cryoprotectant solution. The organotypically cultured skin equivalent is supported on a porous membrane of a tray of the present disclosure, and the tray is placed in a suitable vessel, such as a culture vessel or a tissue container assembly of the present disclosure. A suitable volume of cryoprotectant solution is added to the vessel to be in contact with the porous membrane, but not submerge the tissue, allowing cryoprotectant transfer into the tissue through its base. Certain embodiments of the present invention are not limited to the use of any particular cryoprotectant. In some preferred embodiments, the cryoprotectant is glycerol. The cryoprotectant may be provided in different concentrations in the cryoprotectant solution. In some embodiments, the cryoprotectant is provided in a solution comprising about 20% or 21% to about 70% of the solution by volume, and more preferably about 20% or 21% to about 45% of the solution by volume or 37.5% to 62.5% of the solution by volume, or most preferably from about 25% to 40% of the solution by volume or 42.5% to 57.5% of the solution by volume, depending on the temperature. In some embodiments, the cryoprotectant solution preferably comprises about 32.5% v/v or about 50% v/v cryoprotectant (e.g., glycerol). In some embodiments, the cryoprotectant is provided in a base medium solution. Suitable base medium solutions include, but are not limited to, DMEM, Ham's F-10, Ham's F-12, DMEM/F-12, Medium 199, MEM and RPMI. In some embodiments, the base medium forms the remainder of the solution volume. In some embodiments, the cryoprotectant solution is buffered. Suitable buffers include, but are not limited to, HEPES, Tris, MOPS, and Trizma buffers. Buffering agents may be included at an amount to provide a buffered system in the range of pH 7.0 to 7.4. In some preferred embodiments, the cryoprotectant solution is buffered with from about 5 mM to 15 mM HEPES, most preferably about 10 mM HEPES to a pH of about 7.0 to 7.4.

In some particularly preferred embodiments, treatment with the cryoprotectant solution is conducted in a single step. By "single step" it is meant that the cryoprotectant solution is not exchanged during the equilibration procedure as is common in the art. For example, the treatment step is performed using a cryoprotectant solution with a defined concentration of cryoprotectant as opposed to a stepwise equilibration procedure where several media changes with increasing concentrations of cryoprotectant at each step. In some embodiments, the treatment step is conducted at a reduced temperature. In preferred embodiments, the treatment step is conducted at from about 2 C to 8 C, while in other embodiments, the treatment step is conducted at room temperature, for example from about 15 C to 30 C. In some embodiments, the skin equivalent is incubated in the cryoprotectant solution for about 10 to 60 minutes, preferably from about 20 to 30 minutes.

In some embodiments, the skin equivalent supported on the porous membrane of the tray is frozen following treatment with the cryoprotectant solution, preferably after excess cryoprotectant solution is removed from the skin equivalent, for example by aspirating the solution or moving the treated skin equivalent to a fresh vessel (e.g., a sterile culture vessel or a sterile tissue container assembly of the present disclosure). Accordingly, in some embodiments, the treated skin equivalent supported on the porous membrane of the tray is frozen by exposure to temperatures ranging from about −50 C to −100 C, and most preferably at about −80 C. In some preferred embodiments the tray with the treated skin equivalent is simply placed in a bag or other vessel (e.g., a sterile culture vessel or a sterile tissue container assembly of the present disclosure) and placed in a freezing unit such as a low temperature (e.g., −80° C. freezer) freezing unit. In contrast, it is common in the art to control the rate of freezing either by controlling the temperature in the freezing unit or by placing the tissue to be frozen in a container that allows control of the rate of decrease in temperature.

In some embodiments, the cryopreserved skin equivalent is packaged for long term storage. In some preferred embodiments, the skin equivalent, in its tray, is enclosed with the bottom and top containers as described in detail above. Is some embodiments, the assembly containing the human skin equivalent is sealed, preferably heat sealed in a sterile bag (e.g., a plastic or polymer bag) to provide a primary package. The primary package is then sealed inside a secondary bag, for example a secondary plastic, foil, or Mylar bag. The cryopreserved tissues of the present invention may preferably be stored at low temperature, from about −50 C to about −100 C or lower, preferably about −80 C. The skin equivalents may be preferably stored from about 1, 2, 3, 4, 5 or 6 months and up to 12 or 24 months without a substantial loss of viability.

In a preferred embodiment, an organotypically cultured skin equivalent in its tray, which is inserted into a sterile bottom container of the present disclosure, is treated with a cryoprotectant solution as described above. Excess cryoprotectant solution is removed from the skin equivalent prior to freezing by aspirating the cryoprotectant solution from the bottom container. The treated skin equivalent in its tray is then enclosed with a sterile top container of the present disclosure, thereby forming a tissue container system. Alternatively, excess cryoprotectant solution is removed from the skin equivalent prior to freezing by moving the tray with the treated skin equivalent to a second, sterile bottom container of the present disclosure and then enclosing the tray with a sterile top container of the present disclosure, thereby forming a tissue container system. The tissue container system containing the treated human skin equivalent is then sealed, preferably heat sealed in a sterile bag (e.g., a plastic or polymer bag) to provide a primary package. The primary package may be sealed inside a secondary bag, for example a secondary plastic, foil, or Mylar bag. The primary or secondary bag is then stored at low temperature, from about −50 C to about −100 C, preferably about −80 C. The skin equivalents may be stored from about 1, 2, 3, 4, 5 or 6 months and up to 12 or 24 months without a substantial loss of viability.

In another preferred embodiment, an organotypically cultured skin equivalent in its tray, which is placed in a culture vessel, is treated with a cryoprotectant solution as described above. Excess cryoprotectant solution is removed from the skin equivalent prior to freezing by moving the tray with the treated skin equivalent to a sterile bottom container of the present disclosure and then enclosing the tray with a sterile top container of the present disclosure, thereby forming a tissue container system. The tissue container system containing the treated human skin equivalent is then sealed, preferably heat sealed in a sterile bag (e.g., a plastic or polymer bag) to provide a primary package. The primary package may be sealed inside a secondary bag, for example a secondary plastic, foil, or Mylar bag, to produce a secondary package. The primary or secondary package is then stored at low temperature, from about −50 C to about −100 C, preferably about −80 C. The skin equivalents may be stored from about 1, 2, 3, 4, 5 or 6 months and up to 12 or 24 months without a substantial loss of viability.

In some embodiments, the present invention provides a method of thawing a cryopreserved skin equivalent prior to application to a subject, comprising providing a cryopreserved tissue in the tissue container system as described above, removing the top tissue container to expose the cryopreserved tissue, and filling the reservoir in the bottom tissue container with a liquid medium under conditions that the cryopreserved tissue thaws to provide a thawed tissue, where the cryoprotectant contained within the tissue is diluted into the liquid medium, leaving a tissue that is substantially free of cryoprotectant. In other embodiments, the method comprises removing a primary or secondary package containing a tissue container system comprising a cryopreserved tissue from a freezer or shipping container, removing the tissue container system from the package(s), removing the top tissue container to expose the cryopreserved tissue, and transferring the tray with the cryopreserved skin equivalent from the first tissue container into a second tissue container that is sterile and staged in the sterile field and contains a liquid medium in the container reservoir, such that the transferred cryopreserved tissue thaws to provide a thawed tissue and the cryoprotectant contained within the tissue is diluted into the liquid medium. In some of the above embodiments, the liquid medium is a tissue compatible solution, preferably a buffered solution. Suitable tissue compatible solutions include, but are not limited to, DMEM, Ham's F-10, Ham's F-12, DMEM/F-12, Medium 199, MEM and RPMI. Suitable buffers include, but are not limited to, HEPES, Tris, MOPS, and Trizma buffers. Buffering agents may be included at an amount to provide a buffered system in the range of pH 7.0 to 7.4. In still other embodiments, the tray with the cryopreserved skin equivalent is removed from the tissue container and placed on an absorbent medium to remove thawed cryoprotectant solution from the skin equivalent. The absorbent medium may be in any suitable, preferably sterile, vessel (e.g., a culture vessel or a fresh tissue container assembly). The present invention is not limited to the use of a particular absorbent medium. Suitable absorbent media include, but are not limited to, Telfa® pads, cellulosic pads (e.g., Whatman 1003-090 filter pads and Pall 70010 filter pads), gauze pads, and foam pads (e.g., Covidien 55544 hydrophilic foam pad). In some preferred embodiments, the absorbent medium is a Telfa® pad. In some embodiments, the absorbent medium further comprises a tissue-compatible solution. In some embodiments, the tissue compatible solution is a buffered solution. Suitable tissue compatible solutions include, but are not limited to, DMEM, Ham's F-10, Ham's F-12, DMEM/F-12, Medium 199, MEM and RPMI. Suitable buffers include, but are not limited to, HEPES, Tris, MOPS, and Trizma buffers. Buffering agents may be included at an amount to provide a buffered system in the range of pH 7.0 to 7.4.

It is contemplated that the cryopreserved skin equivalents of the present invention may be used therapeutically after thawing. In some embodiments, the cryopreserved skin substitute is used after thawing in wound closure and burn treatment applications. The use of autografts and allografts for the treatment of burns and wound closure is described in Myers et al., A. J. Surg. 170(1):75-83 (1995) and U.S. Pat. Nos. 5,693,332; 5,658,331; and 6,039,760, each of which is incorporated herein by reference. In some embodiments, the skin equivalents may be used in conjunction with dermal replacements such as DERMAGRAFT or INTEGRA. Accordingly, the present invention provides methods for wound closure, including ulcers or wounds caused by burns, comprising providing a cryopreserved skin equivalent in a tissue container system of the present disclosure, thawing the skin equivalent, and treating a patient suffering from a wound with the thawed skin equivalent under conditions such that the wound is closed.

In some embodiments, the skin equivalents are utilized to treat chronic skin wounds. Chronic skin wounds (e.g., venous ulcers, diabetic ulcers, pressure ulcers) are a serious problem. The healing of such a wound often takes well over a year of treatment. Treatment options currently include dressings and debridement (use of chemicals or surgery to clear away necrotic tissue), and/or antibiotics in the case of infection. These treatment options take extended periods of time and high levels of patient compliance. As such, a therapy that can increase a practitioner's success in healing chronic wounds and accelerate the rate of wound healing would meet an unmet need in the field. Accordingly, the present invention contemplates treatment of skin wounds with cryopreserved skin equivalents. In some embodiments, skin equivalents are topically applied to wounds after thawing. In other embodiments, cryopreserved skin equivalents are used for application to partial thickness wounds after thawing. In other embodiments, cryopreserved skin equivalents are used to treat full thickness wounds after thawing. In other embodiments, cryopreserved skin equivalents are used to treat numerous types of internal wounds after thawing, including, but not limited to, internal wounds of the mucous membranes that line the gastrointestinal tract, ulcerative colitis, and inflammation of mucous membranes that may be caused by cancer therapies. In still other embodiments, skin equivalents expressing host defense peptides or pro-angiogenic factors are used as a temporary or permanent wound dressing after thawing.

In still further embodiments, the cells are engineered to provide additional therapeutic agents to a subject. The present invention is not limited to the delivery of any particular therapeutic agent. Indeed, it is contemplated that a variety of therapeutic agents may be delivered to the subject, including, but not limited to, enzymes, peptides, peptide hormones, other proteins, ribosomal RNA, ribozymes, small interfering RNA (siRNA) micro RNA (miRNA), and antisense RNA. In preferred embodiments, the agents are host defense peptides such as human beta-defensin 1, 2, or 3 or cathelicidin or other proteins such as VEGF and HIF-1 a, see, e.g., U.S. Pat. Nos. 7,674,291; 7,807,148; 7,915,042; 7,988,959; and 8,092,531; each of which is incorporated herein by reference in its entirety. These therapeutic agents may be delivered for a variety of purposes, including but not limited to the purpose of correcting genetic defects. In some particular preferred embodiments, the therapeutic agent is delivered for the purpose of detoxifying a patient with an inherited inborn error of metabolism (e.g., aminoacidopathesis) in which the skin equivalent serves as wild-type tissue. It is contemplated that delivery of the therapeutic agent corrects the defect. In some embodiments, the cells are transfected with a DNA construct encoding a therapeutic agent (e.g., insulin, clotting factor IX, erythropoietin, etc.) and skin equivalents prepared from transfected cells are administered to the subject. The therapeutic agent is then delivered to the patient's bloodstream or other tissues from the graft. In preferred embodiments, the nucleic acid encoding the therapeutic agent is operably linked to a suitable promoter. The present invention is not limited to the use of any particular promoter. Indeed, the use of a variety of promoters is contemplated, including, but not limited to, inducible, constitutive, tissue-specific, and keratinocyte-specific promoters. In some embodiments, the nucleic acid encoding the therapeutic agent is introduced directly into the keratinocytes (i.e., by electroporation, calcium phosphate co-precipitation, or liposome transfection). In other preferred embodiments, the nucleic acid encoding the therapeutic agent is provided as a vector and the vector is introduced into the keratinocytes by methods known in the art. In some embodiments, the vector is an episomal vector such as a replicating plasmid. In other embodiments, the vector integrates into the genome of the keratinocytes. Examples of integrating vectors include, but are not limited to, retroviral vectors, adeno-associated virus vectors, non-replicating plasmid vectors and transposon vectors

EXAMPLES

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); mM (millimolar); µM (micromolar); N (Normal); mol (moles); mmol (millimoles); pmol (micromoles); nmol (nanomoles); g (grams); mg (milligrams); lig (micrograms); ng (nanograms); 1 or L (liters); ml or mL (milliliters); µl or µL (microliters); cm (centimeters); mm (millimeters); pm (micrometers); nm (nanometers); C (degrees Centigrade); U (units), mU (milliunits); min. (minutes); sec. (seconds); % (percent); kb (kilobase); bp (base pair); PCR (polymerise chain reaction); BSA (bovine serum albumin); CFU (colony forming units); kGy (kiloGray); PVDF (polyvinylidine fluoride); BCA (bicinchoninic acid); SDS-PAGE (sodium dodecyl sulfate polyacrylamide gel electrophoresis).

Example 1

StrataGraft® skin tissue is a living, full-thickness, allogeneic human skin substitute that reproduces many of the structural and biological properties of normal human skin. StrataGraft® skin tissue contains both a viable, fully-stratified epidermal layer derived from NIKS® cells, which are a consistent and well-characterized source of pathogen-free human keratinocyte progenitors, and a dermal layer containing normal human dermal fibroblasts (NHDF) embedded in a collagen-rich matrix. StrataGraft® skin tissue possesses excellent tensile strength and handling characteristics that enable it to be meshed, stapled, and sutured similarly to human skin grafts. StrataGraft® also exhibits barrier function comparable to that of intact human skin and is capable of delivering bioactive molecules for wound bed conditioning and tissue regeneration. The physical and biological characteristics of StrataGraft® skin tissue make it ideal for the treatment of a variety of skin wounds.

The manufacturing process for StrataGraft® skin tissue encompasses three sequential cell and tissue culture processes. In Stage I of the manufacturing process, NIKS® keratinocytes are expanded in monolayer cell culture. Concurrent with the NIKS® keratinocyte culture in Stage I, NHDF are expanded in monolayer culture and combined with purified type I collagen and culture medium and allowed to gel to form the cellularized dermal equivalent (DE). Alternatively, NHDF are seeded into Transwell® inserts (Corning) and allowed to proliferate and secrete and assemble extracellular matrix molecules into a simplified dermal equivalent. In Stage II, NIKS® keratinocytes are seeded onto the surface of the DE and cultured under submerged conditions for two days to promote complete epithelialization of the DE surface. The tissue is then lifted to the air-liquid interface in Stage III, where it is maintained for 18 days in a controlled, low humidity environment to promote tissue maturation. The skin equivalents are generally prepared as described in U.S. Pat. Nos. 7,674,291; 7,807,148; 7,915,042; 7,988,959; 8,092,531; and U.S. Pat. Publ. 20140271583; each of which is incorporated herein by reference in its entirety.

Example 2

This example describes improved cryopreservation methods for human skin equivalents utilizing a pre-freeze treatment step with cryopreservation solutions containing 32.5% or 50% glycerol at room temperature and is described in copending U.S. Pat. Publ. 20140271583, which is incorporated by reference herein in its entirety. The general production process is unchanged from the current method described previously. At the end of the production process, the tissues are treated and cryopreserved as follows.

| Parameter | Operating Range |
|---|---|
| Cryoprotectant formulation | 32.5% (v/v) glycerol DMEM (1X) 10 mM HEPES (pH 7.0 to 7.4); or 50% (v/v) glycerol DMEM (1X) 10 mM HEPES (pH 7.0 to 7.4) |
| Pre-freeze cryoprotectant incubation temperature | Room temperature |
| Pre-freeze cryoprotectant incubation time | 15-45 minutes |
| Freeze method | Direct transfer to −80 C. freezer |
| Storage temperature | −70 to −90 C. |
| Shipping conditions | Overnight delivery on dry ice |

All steps of the cryopreservation process prior to the final product packaging step are performed aseptically inside a Class 100 biosafety cabinet in a Class 10,000 cleanroom. The specific volumes and dishes described in this example are applicable to tissues generated in the previous circular, 44 cm$^2$ format, not the larger rectangular format of the current disclosure.

Step 1—Dispense 20 ml of cryoprotectant solution to 100 mm culture dishes.

Step 2—Transfer Transwell® inserts containing StrataGraft® tissues into individual dishes containing cryoprotectant solution. Incubate tissues 15-45 minutes in cryoprotectant solution.

Step 3—Transfer Transwell® inserts containing treated StrataGraft® tissues to new sterile 100 mm culture dishes containing final product label so that the tissue rests on the bottom of the culture dish. Excess cryoprotectant is allowed to drain from the skin equivalent to provide a treated skin equivalent that is substantially free of excess cryoprotectant on the exterior surfaces of the skin equivalent.

Step 4—Heat-seal 100 mm culture dishes in clear, sterile bags. Place primary package into secondary Mylar bag and heat-seal.

Step 5—Remove the packaged StrataGraft® tissues from cleanroom and transfer tissues to an ultralow freezer (−70° C. to −90° C.). Place tissues in a pre-cooled rack in the freezer that allows unrestricted airflow to the top and bottom of the packaged tissues to ensure uniform and rapid cooling. Leave tissues undisturbed overnight during the freezing process.

Cryopreserved tissues were thawed at room temperature for 10 minutes, transferred to a hold chamber containing Telfa® pads saturated with 40 ml of HEPES-buffered culture medium that had been warmed to room temperature (RT), and held at RT for 15 to 20 minutes. Tissues were transferred to a culture dish containing 90 ml of SMO1 medium and returned to culture overnight. Tissues were analyzed for viability after overnight re-culture. Tissues treated with 32.5% glycerol at room temperature for 15 to 45 minutes had acceptable post-thaw viability. Tissues treated with 50% glycerol at room temperature for 15 minutes also had acceptable viability; however, tissues treated with 50% glycerol at room temperature for 45 minutes had unacceptable viability.

Example 3

This study was performed to evaluate the performance of product packaging plasticware, which is a tissue container assembly of the present disclosure, for use as packaging for cryopreserved StrataGraft® tissues. The study evaluated three independent lots of rectangular, 100 cm$^2$ StrataGraft® tissues comparing tissues packaged in the Transwell® growth chamber and those packaged in the tissue containers described herein. For each batch, post-thaw properties of tissues packaged in the tissue containers of the instant invention were evaluated following different hold conditions and compared to those of control tissues using current packaging and thaw/hold procedures. The results of this study demonstrated that tissue containers of the instant invention are suitable for use in transporting and thawing cryopreserved StrataGraft® tissues and that acceptable thawing can be achieved in the sterile field without use of a Telfa® pad.

StrataGraft® skin tissues are produced in batches of 100 cm$^2$ StrataGraft® skin tissues. This larger tissue format and increase in batch sizes put an added emphasis on efficient storage and shipment of the skin tissues. To address that issue, plasticware tissue containers were designed which reduce the volume of the final packaged product by 60% compared to packaging in the Transwell® growth chamber as disclosed in copending U.S. Pat. Publ. 20140271583. In this example, this packaging is introduced into the process following cryoprotectant treatment, immediately before the product is sealed in the foil pouch and transferred to an ultracold freezer for long-term storage. The tissue containers of the instant invention were designed with a 0.75 mm deep reservoir below tissue that can be flooded with hold solution. This design allows the packaging to be used as a post-thaw hold container, which simplifies the preparation of StrataGraft® tissue for clinical use by eliminating the need for a separate hold basin.

This experiment evaluated the post-thaw properties of StrataGraft® skin tissues from three batches, and frozen in either a Transwell® growth chamber or in the tissue containers of the instant invention. In addition, this study evaluated post-thaw hold procedures performed in the tissues containers of the instant invention without the use of Telfa® pads, compared to control hold conditions performed in basins containing Telfa® pads.

| Group | Pre-Freeze Treatment | Packaging | Thaw Condition | Hold Chamber | Hold Solution | Hold Condition |
|---|---|---|---|---|---|---|
| 1 | 37.5% glycerol 20 min at RT | Transwell® Growth Chamber | 10 min at RT | DeRoyal Basin (2-Telfa) | 250 mL Hold Solution Warmed to 35-39° C. | 15-20 min at RT |
| 2 | | Tissue container assembly | | | | |
| 3 | | | | Tissue container assembly (no Telfa®) | 15 mL Hold Solution Warmed to 35-39° C. | |

Batches of 20 rectangular, 100 cm$^2$ StrataGraft® skin tissues were produced using Stratatech's standard processes. Briefly, NIKS® cells and normal human dermal fibroblasts (NHDF) were expanded in monolayer culture. NHDF were thawed and expanded in monolayer. Following expansion, the NHDF cells were harvested and mixed into a type I collagen solution, dispensed to 100 cm$^2$ rectangular trays of the present disclosure (tissue-culture treated polycarbonate membrane, nominal thickness of about 10 microns, nominal pore size of about 0.4 microns), and gelled to create the dermal equivalent layer (DE). After gelling, the DE was submerged in media in a growth chamber and cultured for five days prior to the NIKS® seed. NIKS® were thawed, expanded, and then harvested and seeded onto DE surfaces. Tissues were maintained in submerged culture for two days to allow for attachment and proliferation of NIKS® over the DE surface and then cultured at the air-liquid interface for 18 days to enable complete epidermal differentiation. Transfers of media, NHDF/collagen mixture, and NIKS® suspension to the trays and Transwell® growth chambers were performed using peristaltic pumps.

At the end of the production process, culture media was aspirated and tissues were treated in the Transwell® growth chamber with 50 mL of cryopreservation solution containing 37.5% glycerol for 20 minutes at room temperature (RT) whilst still supported on the membrane of the tray. At the end of treatment, the trays containing the nine tissues designated for this experiment were removed from the excess cryopreservation solution and packaged into one of two packaging configurations: 1) three tissues were kept in the Transwell® growth chamber in the high position and sealed inside of 7.875"×12" foil pouches (Group 1); and 2) six tissues were transferred to sterile tissue containers of the instant invention and sealed inside 6.75"×10.25" foil peel pouches (Group 2 and Group 3, n=3 per group). At the end of packaging, all packaged tissues were transferred to an ultracold freezer and stored at −70 to −90° C. until analysis.

Group 1 and Group 2 tissues were then thawed using previously established procedures that utilized an absorbent medium (e.g., Telfa® pad). Group 3 tissues were thawed using a simplified hold procedure. Briefly, Group 3 cryopreserved tissues were thawed at room temperature for 10 minutes in the tissue container in which the tissue was frozen, the bottom tissue containers were then flooded with hold solution (15 ml of HEPES-buffered culture medium that had been warmed to 35-39 C) and held at room temperature for 15 to 20 minutes. Following the post-thaw hold, tissues from all groups were transferred to new rectangular growth chambers containing SM01 and re-cultured for 22 to 26 hours Tissues were evaluated for appearance, barrier function, viability, histology, and VEGF secretion in the conditioned media. In addition, whole tissue MTT staining was performed to evaluate uniformity of the tissue viability. The results of tissues frozen in the tissue containers of the instant invention (groups 2 and 3) were compared to those of the control group.

Figure 5:
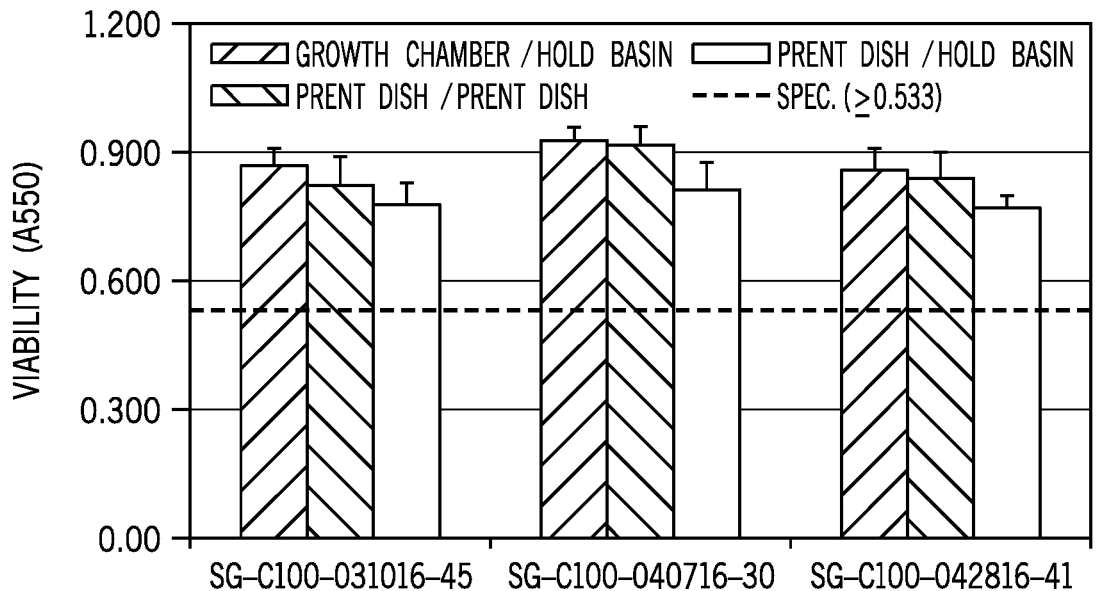
FIG. 5 is a graph of tissue viability after 1-day re-culture. Data are mean±stdev of 15 samples per group (5 samples/tissue×3 tissues/condition in each batch).
Figure 6:
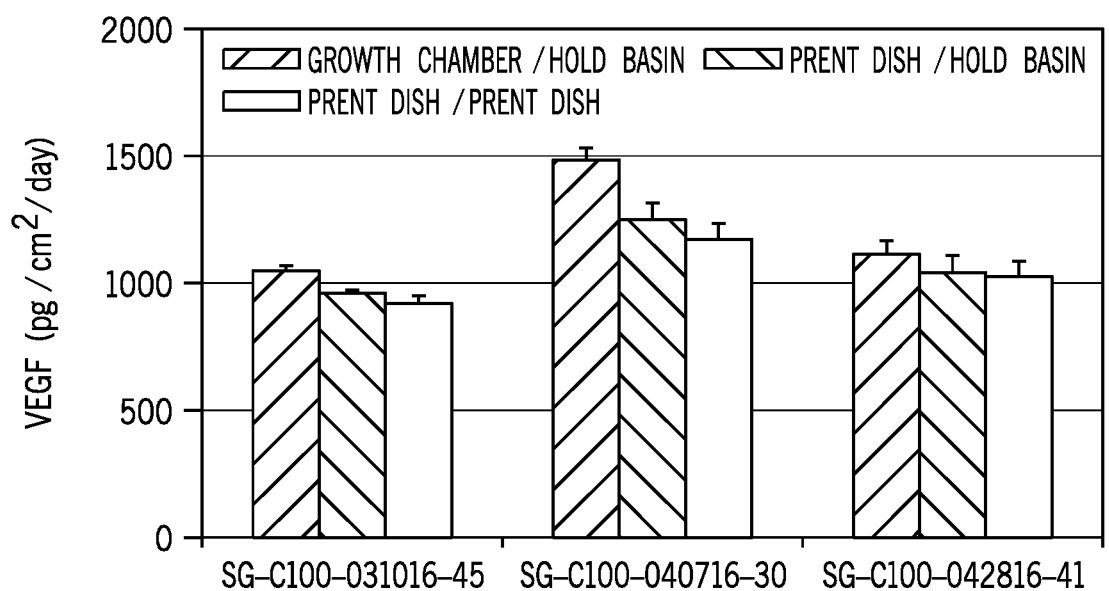
FIG. 6 is a graph of post-thaw VEGF secretion during 1-day re-culture. Data are mean±stdev of 3 tissues per condition in each batch.
Figure 7A:
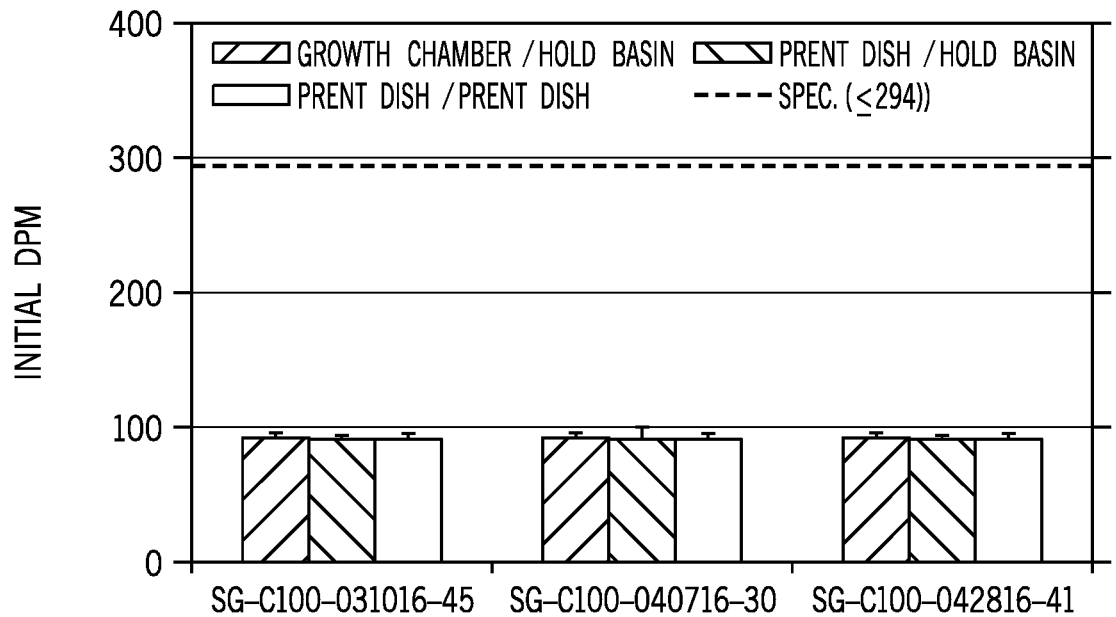
FIG. 7A and FIG. 7B are graphs of post-thaw tissue barrier function after 1-day re-culture with initial DPM (FIG. 7A) and DPM change (FIG. 7B). Data are mean±stdev of 12 reads per group (4 samples/tissue×3 tissues/condition in each batch).
Figure 7B:
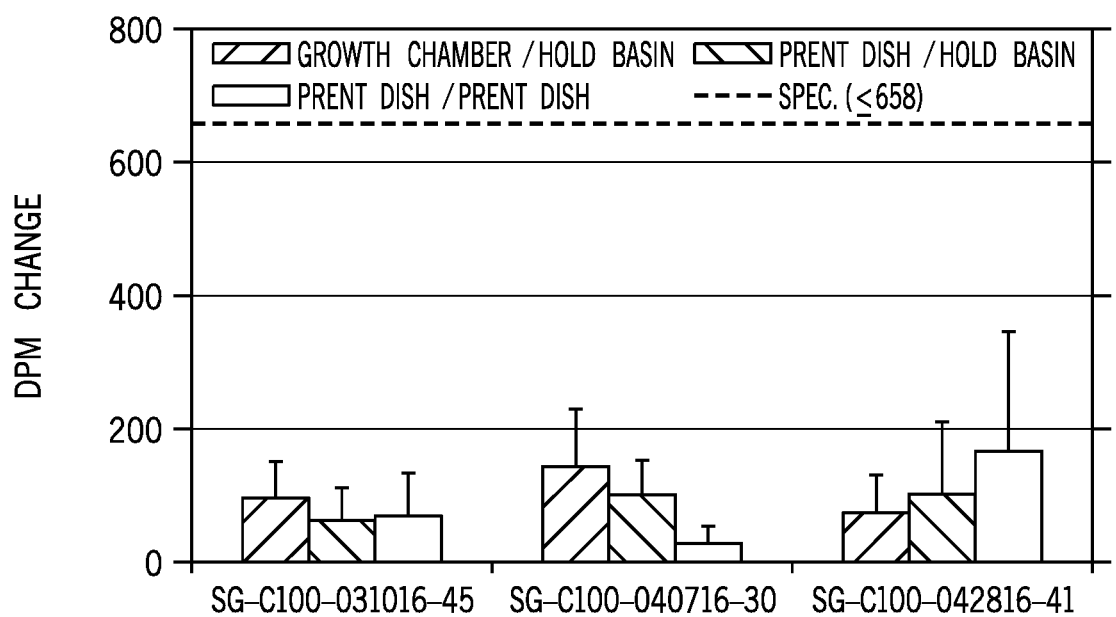

The results of this study demonstrate that use of the tissue containers of the instant invention does not affect the properties of cryopreserved StrataGraft® tissues. Tissues packaged in the two configurations and thawed/held using the previously established procedures (Groups 1 and 2) had comparable appearance, histology, viability, and barrier function, and VEGF secretion. The tissue containers of the instant invention also showed promising results for use in a simplified hold procedure. Tissues packaged and kept in tissue containers of the instant invention for the post-thaw hold (Group 3) had similar properties to both other groups. Tissue appearance, histology, VEGF secretion, and barrier function were not significantly different than control tissues (Group 1); viability showed a modest (−10%), but statistically significant ($p<0.05$), reduction compared to controls, while still easily exceeding the established lot release criterion. MTT staining patterns of tissues from all groups were comparable, with qualitatively consistent staining across the tissue surfaces. See FIGS. 5, 6 and 7.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in tissue culture, molecular biology, biochemistry, or related fields are intended to be within the scope of the following claims.

The invention claimed is:

1. A sterile tissue container comprising:
    a perimeter wall comprising a flange extending therefrom;
    a substantially planar bottom surface, the perimeter wall surrounding the bottom surface defining a dish having a dish length and a dish width;
    at least one ridge projecting from the perimeter wall above the flange, the at least one ridge having a ridge length and a ridge width; and
    at least one space recessed below the flange on the perimeter wall, the recessed space having a recess length and a recess width,
    wherein the bottom surface has a perimeter defined by the perimeter wall and comprising a perimeter ledge extending around the perimeter to provide a reservoir defined by the perimeter ledge and the bottom surface; and
    wherein the perimeter wall has a male end and a female end opposite the male end along the dish length, wherein the at least one ridge is located at the male end of the perimeter wall and the at least one space is located at the female end of the perimeter wall,
    wherein the sterile tissue container is formed from a medical grade plastic.

2. The sterile tissue container of claim 1, wherein the flange comprises one or more tabs extending from the male end of the perimeter wall.

3. The sterile tissue container of claim 2, wherein the flange comprises one or more tabs extending from the female end of the perimeter wall.

4. The sterile tissue container of claim 1, wherein the ridge has a proximal end and the proximal end of the ridge has one or more indents therein.

5. The sterile tissue container assembly of claim 1, wherein the female end is opposite the male end along the dish length, and wherein the at least one ridge and the at least one space are directly adjacent along the dish length.

6. The sterile tissue container of claim 1, wherein the recess length and recess width being operable to receive a corresponding ridge length and ridge width of another sterile tissue container that is rotated such that the at least one ridge of another sterile tissue container faces the at least one space thereby forming an enclosed container.

7. The sterile tissue container of claim 1, wherein the at least one ridge and the at least one space abut along the dish length, and wherein the ridge length plus the recess length equals the dish length.

8. The sterile tissue container of claim 1, wherein the reservoir is 0.75 mm to 1.5 mm deep.

9. A sterile tissue container assembly comprising:
    substantially identical top and bottom sterile tissue containers, each of the top and bottom sterile tissue containers comprising:
        a perimeter wall comprising a flange extending therefrom;
        a substantially planar bottom surface, the perimeter wall surrounding the bottom surface defining a dish having a dish length and a dish width;
        at least one ridge projecting from the perimeter wall above the flange, the at least one ridge having a ridge length and a ridge width; and
        at least one space recessed below the flange on the perimeter wall, the recessed space having a recess length and a recess width;
    wherein the bottom surface has a perimeter defined by the perimeter wall and comprises a perimeter ledge extending around the perimeter to provide a reservoir defined by the perimeter ledge and the bottom surface, and
    wherein the perimeter wall has a male end and a female end, wherein the at least one ridge is located at the male end of the perimeter wall and the at least one space is located at the female end of the perimeter wall,
    wherein each sterile tissue container is formed from a medical grade plastic, and
    wherein when the top sterile tissue container is rotated and placed facing the bottom sterile tissue container, the at least one space on the female end of the bottom sterile tissue container releasably receives the at least one ridge on the male end of the top sterile tissue container, thereby forming an enclosed container.

10. The sterile tissue container assembly of claim 9, wherein when the top and bottom sterile tissue containers are assembled the flanges of the top and bottom containers contact one another.

11. The sterile tissue container assembly of claim 10, wherein the flange comprises one or more tabs extending from the male end of the perimeter wall and one or more tabs extending from the female end of the perimeter wall.

12. The sterile tissue container of claim 11, wherein when the top and bottom sterile tissue containers are assembled, the one or more tabs extending from the male end of the perimeter wall of the bottom sterile tissue container do not overlap with the one or more tabs extending from the female end of the perimeter wall of the top sterile tissue container.

13. The sterile tissue container assembly of claim 9, wherein the reservoir is 0.75 mm to 1.5 mm deep.

14. A sterile tissue container system comprising:
    substantially identical top and bottom sterile tissue containers and a tray comprising a porous bottom surface,
    each of the top and bottom sterile tissue containers comprising:
        a perimeter wall comprising a flange extending therefrom;
        a substantially planar reservoir bottom surface, the perimeter wall surrounding the bottom surface defining a dish having a dish length and a dish width;
        at least one ridge projecting from the perimeter wall above the flange, the at least one ridge having a ridge length and a ridge width; and
        at least one space recessed below the flange on the perimeter wall, the recessed space having a recess length and a recess width;
    wherein the reservoir bottom surface has a perimeter defined by the perimeter wall and comprises a perimeter ledge extending around the perimeter to provide a reservoir defined by the perimeter ledge and the reservoir bottom surface, wherein the tray is sized to be supported by the ledge and above the reservoir bottom surface when inserted into the sterile tissue container, and
    wherein the perimeter wall has a male end and a female end, wherein the at least one ridge is located at the male end of the perimeter wall and the at least one space is located at the female end of the perimeter wall, and
    wherein the sterile tissue container is formed from a medical grade plastic, and
    wherein when the top sterile tissue container is rotated and placed facing the bottom sterile tissue container, the at least one space on the female end of the bottom sterile tissue container releasably receives the at least one ridge on the male end of the top sterile tissue container, thereby forming an enclosed container.

15. The sterile tissue container system of claim 14, wherein when the top and bottom sterile tissue containers are assembled the flanges of the top and bottom containers contact one another.

16. The sterile tissue container assembly of claim 15, wherein the flange comprises one or more tabs extending from the male end of the perimeter wall and one or more tabs extending from the female end of the perimeter wall.

17. The sterile tissue container of claim 16, wherein when the top and bottom sterile tissue containers are assembled, the one or more tabs extending from the male end of the perimeter wall of the bottom sterile tissue container do not overlap with the one or more tabs extending from the female end of the perimeter wall of the top sterile tissue container.

18. The sterile tissue container assembly of claim 14, wherein the female end is opposite the male end along the dish length, and wherein the at least one ridge and the at least one space are directly adjacent along the dish length.

19. The sterile tissue container system of claim 14, wherein the porous bottom surface of the tray is a porous membrane.

20. The sterile tissue container system of claim 14, wherein the ridge has a proximal end and the proximal end of the ridge has one or more indents therein and the tray has one or more tray tabs so that when the tray is inserted into the bottom sterile tissue container the one or more tabs are inserted into the one or more indents.

21. The sterile tissue container system of claim 14, further comprising an organotypic skin substitute supported on the porous bottom surface of the tray.

22. The sterile tissue container system of claim 21, wherein the organotypic skin substitute is cryopreserved.

23. The sterile tissue container system of claim 14, further comprising a sterile package containing the sterile tissue container system.

24. The sterile tissue container system of claim 14, wherein the reservoir is 0.75 mm to 1.5 mm deep.

* * * * *